United States Patent [19]

Jeck

[11] 4,228,105
[45] Oct. 14, 1980

[54] 4-BIPHENYLYL-4-HYDROXYALKAN-2-ONES

[75] Inventor: Rüdiger Jeck, Riehen, Switzerland

[73] Assignee: Sandoz Ltd., Basel, Switzerland

[21] Appl. No.: 964,046

[22] Filed: Nov. 27, 1978

[30] Foreign Application Priority Data

Dec. 1, 1977 [CH] Switzerland ............... 14703/77

[51] Int. Cl.$^2$ ............................................. C07C 49/82
[52] U.S. Cl. ..................................... 568/325; 544/175;
544/395; 546/237; 568/306; 568/315; 568/316
[58] Field of Search ...................................... 260/590 D

[56] References Cited

U.S. PATENT DOCUMENTS

| | | | |
|---|---|---|---|
| 3,859,256 | 1/1975 | Teufel et al. | 260/618 D |
| 3,859,363 | 1/1975 | Teufel et al. | 260/618 D |
| 3,901,927 | 8/1975 | Seeger et al. | 260/346.1 R |
| 4,081,476 | 3/1978 | Anderson et al. | 560/255 |

OTHER PUBLICATIONS

Nickl, et al. "Chem. Abstracts", vol. 82 (1975), No. 155,800C, Abstract Corresponds to U.S. 3,920,668.

*Primary Examiner*—Henry R. Jiles
*Assistant Examiner*—R. W. Ramsuer
*Attorney, Agent, or Firm*—Gerald D. Sharkin; Richard E. Vila; Frederick H. Weinfeldt

[57] ABSTRACT

A process for the production of compounds of formula I,

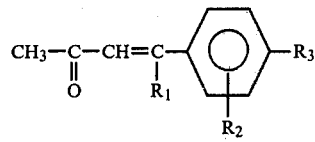

wherein
$R_1$ is alkyl of 1 to 3 carbon atoms,
$R_2$ is hydrogen, fluorine, chlorine or bromine, and
$R_3$ is bromine, iodine, isobutyl, tert. butyl, cyclohexyl, cyclohexenyl; or phenyl, optionally substituted by fluorine, chlorine, bromine or alkoxy of 1 to 4 carbon atoms; or a radical of formula II,

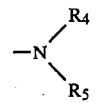

in which either
$R_4$ and $R_5$ are the same or different and each signifies alkyl of 1 to 3 carbon atoms,
or
$R_4$ and $R_5$ together signify the radical —(CH$_2$)$_n$—, in which n is 4 or 5, the radical —CH$_2$—CH$_2$—O—CH$_2$—CH$_2$—, the radical —CH$_2$—CH=CH—CH$_2$—, or the radical —CH$_2$—CH$_2$—N(R$_6$)—CH$_2$—CH$_2$—, in which R$_6$ is hydrogen or alkyl of 1 to 3 carbon atoms. Hydroxyketone and hydroxy imine intermediates are also disclosed.

The compounds of formula I are known to exhibit anti-inflammatory activity.

4 Claims, No Drawings

4-BIPHENYLYL-4-HYDROXYALKAN-2-ONES

This invention relates to a process for the production of phenylbutenones.

More particularly, this invention provides a process for the production of compounds of formula I,

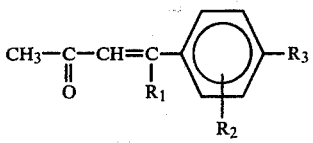
I wherein
$R_1$ is alkyl of 1 to 3 carbon atoms,
$R_2$ is hydrogen, fluorine, chlorine or bromine, and
$R_3$ is bromine, iodine, isobutyl, tert. butyl, cyclohexyl, cyclohexenyl; or phenyl, optionally substituted by fluorine, chlorine, bromine or alkoxy of 1 to 4 carbon atoms; or a radical of formula II,

II in which either
$R_4$ and $R_5$ are the same or different and each signifies alkyl of 1 to 3 carbon atoms,
or
$R_4$ and $R_5$ together signify the radical $-(CH_2)_n-$, in which n is 4 or 5, the radical $-CH_2-CH_2-O-CH_2-CH_2-$, the radical $-CH_2-CH=CH-CH_2-$, or the radical $-CH_2-CH_2-N(R_6)-CH_2-CH_2-$, in which $R_6$ is hydrogen or alkyl of 1 to 3 carbon atoms.

Accordingly, the present invention provides a process for the production of a compound of formula I characterised by dehydrating a compound of formula III,

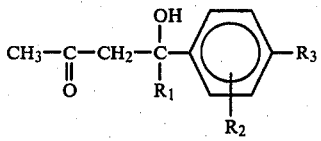
III wherein $R_1$, $R_2$ and $R_3$ are as defined above.

The process is conveniently carried out with dehydrating agents, such as an acid, e.g. sulfuric, hydrochloric, oxalic, acetic, benzenesulphonic or p-toluenesulphonic acid, and in aqueous medium which contains water and a water-miscible solvent, for example a lower alkanol, e.g. methanol, or a cyclic ether, e.g. dioxane. The reaction temperature is suitably from 20° to 100° C.

The compounds of formula III may be produced by hydrolysing a compound of formula IV,

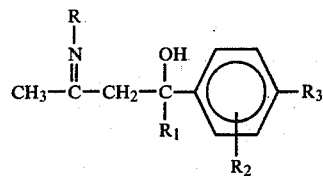
IV wherein
$R_1$, $R_2$ and $R_3$ are as defined above, and
R is cyclohexyl or alkyl with 1-8 carbon atoms.

The hydrolysis may be carried out with an acid, for example as described above for the production of compounds of formula I. The compounds of formula III may be isolated and purified in conventional manner, but they can also be dehydrated in situ, without isolation, to form a compound of formula I.

Accordingly the present invention also provides a process for the production of a compound of formula I which comprises hydrolysing and dehydrating a compound of formula IV as defined above.

The compounds of formula IV may be produced by reacting a compound of formula V,

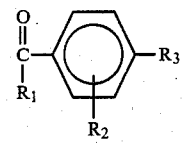
V wherein $R_1$, $R_2$ and $R_3$ are as defined above, with a compound of formula VI,

VI wherein R is as defined above, in the presence of an organo-lithium compound or with a mixture or reaction product of a compound of formula VI and an organo-lithium compound.

The reaction is suitably effected in an inert organic solvent, such as an ether, e.g. diethyl ether or tetrahydrofuran, or a hydrocarbon, e.g. hexane. Preferably the reaction is carried out under an inert atmosphere, for example nitrogen. The reaction temperature is conveniently from −70° to +20° C. Suitable organo-lithium compounds are, for example, methyllithium, n-butyllithium, lithiumdiisopropylamide or lithiumpiperidid, preferable n-butyllithium.

The compounds of formula IV may be isolated and purified in conventional manner, but they need not be isolated and may be allowed to undergo hydrolysis and dehydration in situ to form directly a compound of formula I.

The compounds of formula I, which may exist in the form of geometric isomers, are obtained by the process described above predominately in trans form, for example to the extent of at least 90%, usually at least 95%.

The compounds of formula V and VI are either known or may be produced in conventional manner.

The compounds of formula I are known. They exhibit antiinflammatory activity.

The compound of formula I, wherein $R_1$ is methyl, $R_2$ is hydrogen and $R_3$ is phenyl, is preferred.

EXAMPLE 1

2-(p-Biphenylyl)-2-penten-4-one

A solution of 76.6 g N-isopropyliden-cyclohexyl amine in 230 ml tetrahydrofurane is cooled to −20° C. and treated dropwise with 235 g of 15% n-butyllithium in hexane under nitrogen, maintaining the temperature at −20° C. After the addition is complete, the mixture is stirred for 15 minutes at −20° C. Then 98 g 4-acetyl-biphenyl are added at −20° C. and the mixture is stirred for 2½ hours at −20° C. A mixture of 160 ml concentrated hydrochloric acid and 160 ml water is added, whereby [4-hydroxy-4-(p-biphenylyl)-2-pentyliden]cyclohexylamin hydrochloride precipitates. The solid is filtered off and added to a 40° C. warm mixture of 335 ml water, 300 ml methanol and 28 ml glacial acetic acid, and the whole is stirred 20 hours at 40° C. The resulting solid is filtered off, washed with water and dried to give 4-(p-biphenylyl)-4-hydroxypentan-2-one, m.p. 80°–93° C.

To a 70° C. warm solution of 104.2 g 4-(p-biphenylyl)-4-hydroxypentan-2-one in a mixture of 450 ml methanol and 80 ml water 206 g ca. 65% sulphuric acid is added dropwise and the mixture is stirred 2½ hours at 75° C. After cooling to 25° C. the resulting solid is filtered off, washed with water, then with diluted sodium hydroxide solution, again with water, dried and then recrystallised from toluene to give the title compound, m.p. 134°–136° C.

EXAMPLE 2

In manner analogous to Example 1, employing appropriate starting materials in approximatele equivalent amounts, the following compounds of formula I may be obtained:

(a) 2-(p-tert.butylphenyl)-2-penten-4-one,
(b) 2-(p-bromophenyl)-2-penten-4-one,
(c) 2-(p-cyclohexyl-m-chlorophenyl)-2-penten-4-one, m.p. 58°–59° C.,
(d) 2-(p-isobutylphenyl)-2-penten-4-one, colourless, viscous oil, b.p. (0.02 mm Hg) 98°–100° C.,
(e) 4-(p-biphenylyl)-3-hepten-2-one,
(f) 2-[p-(1'-cyclohexenyl)phenyl]-2-penten-4-one,
(g) 4-(p-cyclohexylphenyl)-3-penten-2-one, m.p. 52°–53° C.,
(h) 4-(p-biphenylyl)-3-hexen-2-one, m.p. 63° C.,
(i) 2-(p-morpholinophenyl)-2-penten-4-one, hydrochlorid form,
(j) 2-[p-(N-methylpiperazinyl)phenyl]-2-penten-4-one, hydrochloride form and
(k) 2-[p-(3-pyrrolinyl)phenyl]-2-penten-4-one, m.p. 165°–166° C., all substantially in trans form.

What we claim is:
1. A compound of the formula:

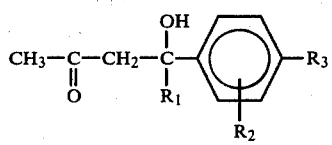

wherein
$R_1$ is alkyl of 1 to 3 carbon atoms,
$R_2$ is hydrogen, fluorine, chlorine or bromine; and
$R_3$ is phenyl or phenyl substituted by fluorine, chlorine, bromine or alkoxy of 1 to 4 carbon atoms.
2. A compound of claim 1 in which $R_3$ is phenyl.
3. A compound of claim 1 in which $R_3$ is substituted phenyl.
4. The compound of claim 2 which is 4-(p-biphenylyl)-4-hydroxypentan-2-one.

* * * * *